Figure 1:
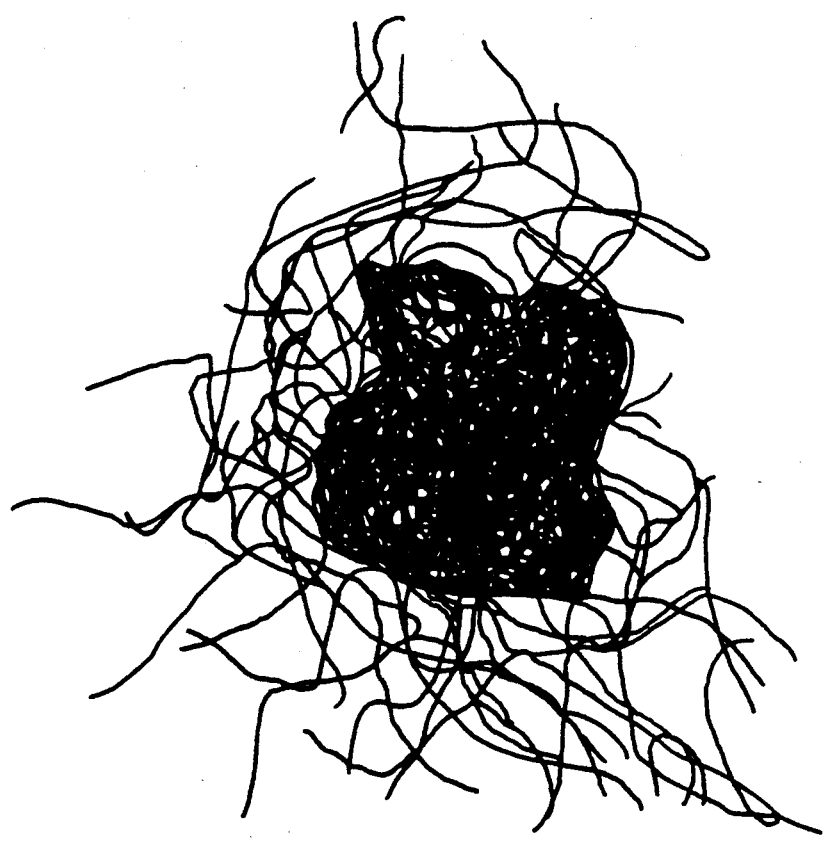

United States Patent [19]

Knack et al.

[11] Patent Number: 5,002,814

[45] Date of Patent: Mar. 26, 1991

[54] SUPERABSORBENT FIBRE FLOCKS, METHODS FOR THEIR PRODUCTION AND APPLICATION

[75] Inventors: Ingo Knack, Schwarzenbek; Wolfgang Beckert, Lutjensee, both of Fed. Rep. of Germany

[73] Assignee: Hanfspinnerei Steen & Co., GmbH, Hamburg, Fed. Rep. of Germany

[21] Appl. No.: 130,005

[22] Filed: Dec. 8, 1987

[30] Foreign Application Priority Data

Dec. 8, 1986 [DE] Fed. Rep. of Germany ....... 3641893
Sep. 21, 1987 [DE] Fed. Rep. of Germany ... 8712723[U]

[51] Int. Cl.$^5$ ..................... A61F 13/15; A61F 13/46; B32B 5/16; B32B 5/30
[52] U.S. Cl. ......................................... 428/85; 47/81; 210/242.4; 210/502.1; 210/504; 210/505; 428/6; 428/86; 428/90; 428/95; 428/97; 428/369; 428/402; 428/542.8; 604/365; 604/370; 604/372; 604/376; 604/385.1
[58] Field of Search ................... 428/6, 85, 86, 90, 95, 428/97, 369, 542.8, 402; 47/81; 210/502.1, 504, 505

[56] References Cited

U.S. PATENT DOCUMENTS

| | | | |
|---|---|---|---|
| 3,901,236 | 8/1975 | Assarsson et al. | |
| 3,922,455 | 11/1975 | Brumlik | 428/85 |
| 4,418,103 | 11/1983 | Tani et al. | 428/90 |
| 4,458,042 | 7/1984 | Espy | 524/14 |
| 4,477,522 | 10/1984 | Sheehan | 428/369 |
| 4,555,421 | 11/1985 | Yasue | 428/6 |
| 4,681,789 | 7/1987 | Donovan et al. | 428/65 |
| 4,721,647 | 1/1988 | Nakanishi et al. | 428/913 |

FOREIGN PATENT DOCUMENTS

| | | |
|---|---|---|
| 0047009 | 3/1982 | European Pat. Off. . |
| 0156257 | 10/1985 | European Pat. Off. . |
| 0174775 | 3/1986 | European Pat. Off. . |
| 2846593 | 8/1979 | Fed. Rep. of Germany . |
| 3002136 | 7/1981 | Fed. Rep. of Germany . |
| 2158718 | 11/1985 | United Kingdom . |

*Primary Examiner*—James C. Cannon
*Attorney, Agent, or Firm*—Michael N. Meller

[57] ABSTRACT

The invention relates to superabsorbent fibre flocks comprising a core of absorptive polymer wherein short polymer fibres have been embedded, such short polymer fibres protruding at least partially from the core. Such superabsorbent fibre flocks can be produced by binding absorbent polymer particles to each other and to the polymer fibres with the aid of a bonding agent and by grinding the fibre flocks thus obtained to the required particulate size. The superabsorbent fibre flocks according to the invention can be used to advantage in sanitary products, especially in baby diapers, menstrual pads and incontinence articles and have further application in separating water and aqueous components from hydrophobic liquids.

21 Claims, 1 Drawing Sheet

SUPERABSORBENT FIBRE FLOCKS, METHODS FOR THEIR PRODUCTION AND APPLICATION

Highly absorptive polymer products are used to remove aqueous liquids and bind them to a solid phase. Such materials are used preferably to produce sanitary products designed to soak up aqueous liquids such as blood or urine and thus prevent the latter from discomforting the wearers of such articles.

Known powdery granulates of weakly cross-linked polymerisates have until the present been incorporated in sanitary products which, in addition to featuring absorbent polymers, exhibit matrix structures consisting generally of cellulose tissue. Such a matrix structure, therefore, will in the present application also be referred to as a fluffy layer.

It has been demonstrated that in the production of sanitary articles it is quite difficult to correctly determine the amount of absorbent polymer product to be inserted, for the polymer product is during production of the sanitary article continuously being drawn into the matrix structure being formed (fluffy layer).

It has furthermore been observed that, during packaging and transportation of the finished product, the absorbent polymer material migrates or is displaced to a considerable degree, the result of which being that such products may either deform in an undesirable way or alternatively, a portion of the absorbent polymer product may not be available when needed.

Thermally bonded polyethylene fibre flocks suitable for use in absorption products, such as diapers, are produced by the Hercules Company of Wilmington, U.S.A. and marketed under the Trade Mark Pulpex ®. The thermally bonded polyethylene fibre matrix structure is supposed to be able to better retain superabsorbent powder.

A wood fluff pulp, obtained by melting a polyolefin mash, is described in EP-A1 123 414 and in the corresponding U.S. Pat. No. 4,458,042.

A sanitary article containing a super water absorbing polymer arranged between two layers of cellulose flocks, is described in DE-OS No. 35 11 805. The absorptive capacity can be increased by changing the thickness of the wadding.

DE-OS No. 36 17 881 describes an absorptive article produced from a base material consisting of fibres that are at least partially hydrophobic, and a water absorbing polymer present at least partially in the form of spheroidal particles and bonded to the surrounding fibres. Such polymerous particles are diffused throughout the fibre material and bonded to the fibres in the form of spherical or ellipsoidal beads arranged serially as in a string of pearls. This known article is produced by placing an aqueous solution of a water-soluble ethylene unsaturated monomer onto the base material consisting of hydrophobic fibres in such a way that some droplets of solution surround and adhere to the fibres; the monomer polymerizes, producing the water-absorbent polymer and the resulting article is left to dry. Such articles therefore retain the shape of the fibrous base material, in which individual droplets of the water-absorbent polymer remain. This process cannot be used to produce flocks easily worked into differently shaped articles.

The object of the present invention is to make available a highly absorbent polymer particulate that can be treated like a powder and yet remain immovable inside the fluffy layers of sanitary articles, whereby the disadvantages related to the known polymer products can be avoided.

The polymer product according to the invention features high absorptive capacity and a particulate structure which permits numerous short fibres to be contained within the individual polymer particles, whereby in particular the ends of the short fibres extend outwardly from the polymer particles. The protruding fibre portions i.e. ends promote interaction between the polymer products according to the invention and the fluffy layer, so that during their incorporation, the polymer products can be fixed individually inside the matrix. The absorbing polymer is present in the form of numerous small particles that form the centre of a given fibre flock formation.

The object of the invention is thus the development of superabsorbent fibre flocks consisting of a core produced from an absorbent polymer in which are embedded short polymer fibres, which protrude at least partway from the core.

In the preferred embodiment, the core of the superabsorbent fibre flocks according to the invention consists of particles of the absorbent polymer which are bound to polymer fibres by means of a bonding agent.

The polymer material applied according to the invention must be capable of absorbing as large an amount of aqueous liquid as possible. Generally speaking, the polymerisates preferred for this role are based on acrylic acid/sodium acrylate. In addition, polymerisates based on cross-linked polymers can be used within the framework of the present invention. Examples of such polymers are cross-linked polysaccharides, such as e.g. carboxymethylcellulose or starch ether, and inorganic, porous materials such as zeolite.

The absorbent polymer particles feature in general a particulate size of 1–1000 microns, preferably 100–630 microns.

As a rule, the polymer material employed should be capable of soaking up many times its own weight in water; the preferred acrylic acid/sodium acrylate polymer in this case can take up at least three times its own weight in water, which renders the polymer jelly-like.

A polyacrylate product particularly suitable within the context of the invention is the commercially available FAVOR ® SAB 922 (Stockhausen Co.). It features the following chemical characteristics:

Chemical base: Sodium polyacrylate
Form: White granules
Grain size: 100–630 microns
Density when packed: 690+30 g/l
Flow behaviour: free flowing
Dry matter: 95+2%
pH value: 6.0+1
(0.1% Gel in 0.9% NaCl)
Storage: Will keep for 1 year under dry conditions Sodium polyacrylate is a weakly linked polymerisate based on acrylic acid/sodium acrylate.

When absorbing water, such preferred polymer material turns without disintegrating into a largely dry and granular gel.

Polymer fibres used are polyolefin fibres, especially polyethylene (PE-) and polypropylene (PP-) short-staple fibres. Such fibres are produced according to a known process and feature preferably a length between 0.2 mm and 10 mm and in particular a length of from 0.5 mm to 4 mm. In general, such fibres feature a titer of 0.5–6 dtex, whereby a titer of 0.7–4 dtex is preferable.

Slight variations in fibre length do not negatively affect the application of the material. It can even be advantageous to purposely employ fibres of various lengths so as to improve the adhesion of the polymer product within the fluffy layer.

Even though, in the context of the present invention, other fibres such as those occuring naturally, e.g. cellulose fibres, glass fibres or fibres of different synthetic materials, preferably fibres of polyester, polyamide and polyacrylnitrile, could be used, the above-mentioned PE and PP short-staple fibres are preferred, since these fibres due to their molecular structure act like a wick and are thus able to transfer liquid from the source point to the highly absorbent polymer material.

In order to improve the adhesive quality of the fibre-containing, highly absorbent polymer product, it would be advantageous to specially treat such fibres in such a way as to cause the latter to wrinkle slightly and thus improve mechanical interaction between such fibres and the fibres of the matrix structure in which the polymer particles according to the invention reside. Another such optional processing step could be that of stretching the fibres before cutting.

In general, two processes are proposed for producing the materials according to the invention.

(a) The polymer product with high absorptive capacity is mixed with the fibres and bonding accomplished through the addition of a bonding agent. The type of bonding agent used depends as much upon the type of polymer product employed as it does upon the type of fibre used. Guided by the chemical composition of the absorbent polymer material and that of the fibres, the technician is able to select a bonding agent that will ensure a reliable bond between the above-named components. The bonding agents must, furthermore, not feature any undesirable secondary effects related to end use in question. If, for instance, the polymer products are to be used in sanitary items such as diapers, the bonding agent selected must not present any danger to health.

Among the numerous known bonding agents which can be used within the framework of the present invention, ethylene/acrylamide copolymers; polymer isocyanates or reactive silicon-organic compounds are preferred, whereby ethylene/acrylic acid copolymers are especially preferred.

The addition of a bonding agent may be left aside, if through the dispersion of the polymer product gel has developed in the peripheral zones of the granular polymer product, and if thereby a sufficiently solid bond can be effected between the polymer product and fibres.

(b) Another method of bonding the fibre material to the polymer product consists of placing the fibre material in the polymer solution before the polymer material is finished, whereupon a linking reaction occurs. This causes the fibres to become at least partially enveloped by the polymer product, and in such a way that the fibre ends combine with the insides of the polymer product. By this means, a product can be produced wherein the fibre ends are located within the polymer, which permits a more rapid and effective transfer of the liquid to the polymer, since the fibres, as explained, act like a wick.

This process permits oil-in-water polymerization to take place.

The ratio of fibres used to the highly absorbent polymer product can in quite a few application areas vary from 10:1 to 1:10. A preferred weight ratio of fibres to highly absorbent polymer product can range between 1:1 and 1:10, in particular from 1:2 to 1:8. In this manner, product variations can be achieved ranging from cotton wadding-and-flock-like to essentially granular polymer products.

After the polymer granules have adhered to each other and to the fibres, small to medium-sized fibre flocks are obtained, minced in a beater mill and then dried.

The finished product thus consists of many small fibres wrapped inside individual polymer particles, which fibres protrude from the latter.

Shown in the illustration is a superabsorbent flock according to the invention. The core consisting of an absorbent polymer and the polymer fibres protruding therefrom, is clearly indicated.

Employment of the highly absorbent fibre-containing polymer products according to the invention greatly simplifies the manufacture of the end product, particularly if the latter is a hygiene product.

Due to their structure according to the invention, the polymer products according to the invention can, during manufacture of the hygiene products, be added in carefully measured amounts, since effective interaction takes place between the product according to the invention and the matrix of the sanitary product. The absorbent polymer product is, by virtue of the structure of the new product, prevented from falling either through or out of the finished product. Because the introduced material almost completely remains inside the finished material, the amount to be added can be regulated so as to reduce the risk of unnecessary loss.

The completed sanitary product must, until it arrives at the place of its end use pass through various transportation and storage phases. Under such conditions, ideally, the form and composition of the final product should not change. A relatively solid bond of the polymer product to the other components of the sanitary product, namely the matrix structure, can be obtained solely by virtue of the fibre-containing polymer product according to the invention.

The wick effect produced by the preferred fibres widens the zone across which individual polymer particles can actively absorb aqueous liquid. The invention enables the use of commercially available superabsorbent products according to a method that obviates the disadvantages associated with a powdery structure. The superabsorbent flocks according to the invention can replace cellulose fluff and improve the absorptive qualities of the superabsorbent polymers and of fluff while combining them with the migration stability of fluff and the simple handling and dispensing properties of superabsorbent powders.

From a medical point of view, the products according to the invention feature one advantage not offered by known products. Because fibreless polymer products are easily displaced, the latter can not only leak out of the finished product during transportation, but during wearing may issue from the finished product onto human skin or sensitive mucous tissues to cause inflammation or immunologically determined irritation. The products according to the invention, by contrast, are fixed inside the fluffy layer and cannot, therefore, enter into direct contact with human skin.

To the polymer products according to the invention may also be added microbicidal agents such as substances that behave like fungicides, in order for example to prevent fungal infections, which may present serious problems in infants.

It is preferable to employ the polymer products according to the invention in the production of sanitary products and incontinence articles. Such articles are preferably baby diapers, menstrual pads, clothing inserts and incontinence pads for adults.

A further area of application forseen for the polymer product according to the invention is that of removing water from hydrophobic liquids. In this connection, the fibre flocks according to the invention are embedded within a filter matrix, and the water-containing hydrophobic liquid to be filtered is poured through the filtration system. Such hydrophobic liquids may be organic solvents or fuels, e.g. kerosone, diesel oil or hydraulic fluid.

EMBODIMENT EXAMPLES

Raw Materials

Highly absorptive polymer product (Favor SAB 922); powdered sodium polyacrylate having a granule size of between 100 and 630 microns.

Polyethylene (PE) and polypropylene (PP) fibres (Steen) having a titer of 2.0 or 2.8 dtex and a staple length of 2 mm.

Bonding agents: Dispersion solution (Primacor 4983 from Dow Chemical) with a 25% ethylene/acrylic acid copolymer content. Dilution: To 20 ml of the 25% dispersion add distilled water up to 100 ml.

EXAMPLE 1

3 g PE fibre (2.8 dtex, 2 mm staple length) and 6 g polymer powder were poured into a 250 ml beaker, 6.8 g of the diluted dispersion solution was added and vigorously mixed with a glass rod. Because the polymer granules adhered to each other and to the fibres, small to medium sized fibre flocks were obtained, which were then minced inside a beater mill (ground for approx. 30–60 sec.)

After the product was dried at a slightly higher (50°–60° C.), a soft, flocklike product was obtained.

EXAMPLE 2

2.0 g PE fibres (titer 2.8 dtex, staple length 2 mm), 6 g of powdered polymer and 4.7 g of diluted dispersion solution, as described in Example 1, were processed.

Result: loose, flocky, more granular product.

EXAMPLE 3

0.5 g of finely cut viscose (cellulose fluff) was thoroughly mixed with 2.5 g of PP fibre (Titer 2.0 dtex, staple length 2 mm), then 6 g of powdered polymer and 8 g of the diluted dispersion were added and processed as in Example 1.

Result: very soft, flocky product with predominantly fine granular polymer particles.

We claim:

1. Superabsorbent fiber flocks comprising a core of superabsorbent polymer particles in which are embedded short polymer fibers that protrude at least partially from the core, wherein the superabsorbent polymer particles are bound to each other and to the polymer fibers by means of a bonding agent, the absorbent core polymer is an acrylic acid/sodium acrylate polymer, carboxymethylcellulose or a starch ether and the polymer fibers are polyolefin fibers.

2. An article of manufacture comprising superabsorbent fiber flocks as defined in claim 1, for separating water and aqueous components from hydrophobic liquids.

3. An article of manufacture comprising superabsorbent fiber flocks as defined in claim 1, for use in plant irrigation systems in gardening and agriculture.

4. Superabsorbent fiber flocks according to claim 1, wherein the bonding agent is an ethylene/acrylic acid copolymer.

5. Superabsorbent fiber flocks according to claim 1, wherein the polymer fibers are polyethylene or polypropylene short staple fibers.

6. Superabsorbent fiber flocks according to claim 5, wherein the polymer fibers have a length of from 0.2 to 10 mm.

7. Superabsorbent fiber flocks according to claim 6, wherein the polymer fibers have a length of from 0.5 to 4 mm.

8. Superabsorbent fiber flocks according to claim 6, wherein the bonding agent is an ethylene/acrylic acid copolymer.

9. An article of manufacture comprising superabsorbent fiber flocks as defined in claim 5, for separating water and aqueous components from hydrophobic liquids.

10. An article of manufacture comprising superabsorbent fiber flocks as defined in claim 5, for use in plant irrigation systems in gardening and agriculture.

* * * * *